United States Patent [19]

Piper

[11] Patent Number: 6,159,505
[45] Date of Patent: Dec. 12, 2000

[54] COMPOSITIONS FOR THE TREATMENT OF MIGRAINE, CONTAINING POTASSIUM, MAGNESIUM AND PYRIDOXINE

[76] Inventor: Edwina M. Piper, Balgowan Cottages, By Leven, Fife, United Kingdom, KY8 5NJ

[21] Appl. No.: 08/945,606

[22] PCT Filed: Jan. 24, 1997

[86] PCT No.: PCT/GB97/00213

§ 371 Date: Jan. 21, 1998

§ 102(e) Date: Jan. 21, 1998

[87] PCT Pub. No.: WO97/26897

PCT Pub. Date: Jul. 31, 1997

[30] Foreign Application Priority Data

Jan. 24, 1996 [GB] United Kingdom .................. 9601398

[51] Int. Cl.⁷ .......................... A61K 33/00; A61K 33/06; A61K 33/08; A61K 33/10; A61K 33/12; A61K 33/14; A61K 31/4415

[52] U.S. Cl. ...................... 424/679; 424/195.1; 424/466; 424/601; 424/602; 424/630; 424/637; 424/639; 424/641; 424/646; 424/665; 424/670; 424/682; 424/683; 424/686; 424/688; 424/689; 424/692; 424/697; 424/717; 424/722; 514/52; 514/165; 514/249; 514/251; 514/276; 514/345; 514/355; 514/387; 514/419; 514/456; 514/457; 514/458; 514/464; 514/474; 514/563; 514/570; 514/574; 514/629; 514/630; 514/904; 514/905

[58] Field of Search ................ 514/345, 52, 165, 514/249, 251, 276, 355, 387, 419, 456–458, 464, 474, 563, 570, 574, 629, 630, 904, 905; 424/682, 683, 686, 688, 692, 663, 709, 715, 717, 722, 195.1, 466, 601, 602, 630, 637, 639, 641, 646, 665, 670, 679, 697

[56] References Cited

U.S. PATENT DOCUMENTS

| 4,542,026 | 9/1985 | Rios | 514/345 |
|---|---|---|---|
| 4,687,782 | 8/1987 | Brantman | 514/561 |
| 4,721,716 | 1/1988 | Neesby | 514/251 |
| 5,053,396 | 10/1991 | Blass | 514/45 |
| 5,108,767 | 4/1992 | Mulchandani et al. | 426/72 |
| 5,292,538 | 3/1994 | Paul et al. | 426/74 |
| 5,397,786 | 3/1995 | Simone | 514/300 |
| 5,770,215 | 6/1998 | Moshyedi | 424/440 |
| 5,939,076 | 8/1999 | Allocca | 424/400 |

OTHER PUBLICATIONS

Druglaunch Abstract 94:13801, abstracting Drug Launches, Jan. 13, 1986.
Druglaunch Abstract 95:836, abstracting Drug Launches, Jan. 23, 1995.
Druglaunch abstract 94:19703, abstracting Drug Launches, Jun. 1, 1987.
Druglaunch Abstract 94:66999, abstracting Drug Launches, Sep. 19,1994.

*Primary Examiner*—Joh Pak
*Attorney, Agent, or Firm*—Nixon & Vanderhye

[57] ABSTRACT

Compositions for the treatment and prevention of migraine or stress headaches wherein there is supplied a combination of potassium, magnesium and pyridoxine optionally in association with other nutrients and/or simple analgesics.

12 Claims, No Drawings

COMPOSITIONS FOR THE TREATMENT OF MIGRAINE, CONTAINING POTASSIUM, MAGNESIUM AND PYRIDOXINE

This application is a 371 of PCT/GB97/00213, filed on Jan. 24, 1997.

FIELD OF INVENTION

This invention relates to novel treatments for migraine which the inventor believes is triggered by a stress reaction.

BACKGROUND

At the onset of the stress reaction the pituitary gland (triggered by the hypothalamus) initiates protective action by secreting the adrenocorticotropic hormone ACTH.

This hormone is transported in the blood to the adrenal glands, which immediately respond to deal with this stress emergency signal, by producing cortisol and aldosterone.

Under non-stress conditions the adrenal glands utilise certain vitamins and minerals in order to function. In order to respond to stress they need an increased supply of vitamins and minerals. These additional supplies are rapidly used up in the stress response reaction. Therefore the adrenal glands ability to resist stress is dependent upon the supply of these "activator" nutrients. If stress is prolonged, or chronic, ultimately the adrenal glands will exhaust themselves through the lack of readily available activator nutrients. Some nutrients are particularly susceptible to depletion.

Vitamin $B_6$ (pyridoxine) is needed by the adrenals and in protein synthesis and in manufacture of vitamin $B_3$. If used in quantity to manufacture $B_3$ to counteract stress, less is available to the adrenals or for protein synthesis. Additional supplies of vitamin $B_6$ are "stolen" from any available sources to answer stress demands. As another part of the stress response mechanism, intracellular potassium, lost from the body in the urine in response to aldosterone, is replaced by potassium held in store within the muscle tissues and bones. There is an overall potassium depletion. Cortisol, produced with aldosterone during the stress reaction, requires a range of nutrients to exert its effects, but particularly vitamin $B_6$ and potassium. Histamine may be produced as a consequence of the stress response. Histamine production can be one of the features of a migraine attack.

As a result of sustained stress, the blood sugar level rises markedly to meet the immediate need but then may drop significantly as a condition of adrenal exhaustion is precipitated. At this point cortisol ceases to rapidly stimulate conversion of protein into sugar and cannot keep pace with the stress induced sugar demands. This may result in hypoglycaemia which also may be a feature of migraine attacks.

As a further stress response, aldosterone is also secreted by the adrenal glands in abnormally large amounts. This immediately triggers the kidneys to retain salt and water while losing potassium.

Consequences of this process may be an elevation of the blood pressure and the expulsion of intracellular potassium. This loss of potassium from cells may cause many adverse consequences since all tissues of the body, especially muscles and nerves, require a normal cellular potassium balance. The sodium retention and potassium loss may cause elevation of blood pressure and acidosis which also can be features of a migraine attack. The potassium loss may be particularly important.

The body relies upon vitamins and minerals for the efficient functioning of the nervous system. Many act in a synergistic mode and cannot function fully without the help of other contributory elements. A lack of one affects all.

A number of vitamins and minerals play multiple roles in the stress response and act in concert to deal with stress. For example, vitamin $B_5$ and vitamin C which may be used to help counteract stress, are also prime activators of the adrenal glands. Vitamin $B_6$ is vital for the nervous system, and essential to the adrenal glands. The B vitamins are synergistic and all may need to be given in order to be fully functional. Vitamin C requires bioflavonoids for optimum efficiency.

Furthermore, in order to exert many of its functions, vitamin $B_6$ requires the presence of the mineral magnesium. Magnesium is also essential to normal adrenal gland function. Magnesium can be an anti-stress nutrient, capable of reducing aldosterone production, thereby preventing the kidneys from retaining salt and water and continuing to drive out potassium.

Migraine is a reaction to stress which occurs in some people and which can be triggered in all stages of the stress response cycle. Many of the biochemical conditions which are induced by stress may cause certain symptoms which are considered to be intrinsic to a migraine attack. The stress and migraine responses appear to progress in a similar way.

Migraine attacks may be the results of stresses upon the body. The stress can be emotional, hormonal, an allergic reaction (including food allergy), poisoning from toxic substances such as tobacco and alcohol, paint fumes and chemical gases (e.g. combustion engine exhaust emissions, gas and coal burning boiler fumes), a response to irregular meals or exercise, or a response to changes in the weather. Temperature sensitivity can also trigger migraine. In some cases, the stress is physical, resulting from physical abnormalities in the body's muscular or skeletal structure, often caused by accident or injury or excessive use.

In a migraine attack, most but not all sufferers first experience early warning symptoms which signal the commencement of a full blown migraine attack. All the senses are affected, but all sufferers do not experience all forms of sensory deviation. This phase is thought to occur as the blood supply to the brain is restricted. There is sometimes a reduction in urine flow.

Vision

A very common phenomenon is the visual corona which registers upon the retina, often taking the form of a sparkling coloured zigzag "halo" which distorts the vision. Another visual signal can be patches of distortion within the field of vision (somewhat akin to looking through a rain spattered pane of glass). Some people develop acute sensitivity to light, or other less common visual symptoms.

Taste

Some sufferers experience a "sweet taste" upon their palate when no sugar is present, or some other taste distortion.

Hearing

Some sufferers experience tinnitus (ringing of the ears) or a certain loss of sound definition. Sometimes there is acute sensitivity to sound.

Touch

Some experience"tingling" sensations often in the face and extremities, some lose feeling altogether (parasthesia—temporary paralysis).

Other Symptoms

Dizziness, loss of balance, nausea, vomiting, sugar craving, stomach pain, sudden fatigue or sudden irritability with no apparent cause, are also premonition symptoms.

Whatever form of early warning occurs, there follows a second stage of the attach. It may follow on immediately or after a hiatus period when no symptoms of any kind are experienced until the second stage commences. This "rest period" usually lasts from 10 minutes up to an hour but can last up to 24 hours.

Once the attack enters the second stage, all of the early warning symptoms can develop further, almost always accompanied by extreme head pain. Some people have to lie in a darkened room, excluding all light and any movement to quell pain and vomiting.

This second stage can have a duration of a few hours or several days.

While the sensory disorientation experienced by migraine sufferers appears to be a direct effect of impaired blood supply to the relevant receptors within the brain, other migraine symptoms correlate with the stages of stress response. I therefore conclude that the migraine cycle and the stress response are closely related.

One medical response to migraine is to attempt to eliminate the cause of migraine (if this is known). This is most easily ascertained if the cause is a definite food allergy such as cheese, wine or chocolate but this approach is not often successful.

If elimination proves unsuccessful then the only medical alternative is pain control or drug therapy to try to block the occurrence of migraine by drugs which act on neurotransmitters associated with stress such as serotonin and catecholamines or by analgesics. The pain of migraine is very difficult to eradicate. The strongest drugs commonly prescribed for migraine have to be given at near toxic levels to be at all efficacious. Most drugs, administered in "safe" doses are unable to completely relieve head pain. Even with the best of modern therapy many patients obtain only partial relief from their attacks.

The Invention

The invention is set out in the claims herein but simply stated the inventor has devised a method of treating migraine which involves the supply of three key ingredients, potassium, magnesium and pyridoxine. These three ingredients are effective alone but optionally may be combined with other nutrients and/or simple analgesics. Whether or not the theory on which the formulation is based is correct, the inventor has found this approach to be effective in treating migraine.

the present invention thus in one aspect provides a composition for use in combating by preventing or treating the effects of migraine, said composition comprising potassium, Vitamin $B_6$ and magnesium, as essential ingredients. Optionally these three essentials may be combined with other nutrients and/or simple analgesics.

The term "composition" is used herein to include separate formulations which are intended for co-administration, either sequentially or simultaneously. It is generally more convenient however for the composition to be in a single admixture formulation.

In one embodiment, the composition comprises the active ingredients in amounts as follows, provided in the form of any appropriate salt or other derivative as well known to those skilled in the art:

| | |
|---|---|
| Potassium | 10 mg to 5000 mg, preferably 100 mg to 1000 mg and very preferably 300 mg to 600 mg. |
| Vitamin $B_6$ | 0.1 to 200 mg, preferably 1 mg to 100 mg and very preferably from 4 mg or 5 mg up to 30 mg. |
| and | |
| Magnesium | 1.0 to 1000 mg, preferably 10 mg to 500 mg, very preferably 20 mg to 300 mg. |

The composition may provide the three primary active ingredients alone or may provide these three together with other minerals and vitamins important in the stress response including calcium, phosphorus, iron, iodine and the water soluble vitamins vitamin $B_1$, vitamin $B_2$, vitamin $B_3$, vitamin $B_5$, vitamin $B_{12}$, folic acid, biotin, bioflavonoids and vitamin C. Optionally said composition may further comprise therapeutically effective amounts of copper, manganese and/or zinc. Tryptophan, which is a precursor of serotonin, which may be depleted in a migraine attack may also be included, preferably without other amino acids.

The formulation preferably does not contain any fats or fat soluble vitamins and it omits carbohydrates other than excipients and sweeteners; it is certainly not in any sense nutritionally complete and is thus not intended as a supplement for nutritional purposes.

Simple analgesics which may be included in the formulation includes aspirin (10–2000 mg), paracetamol (acetaminophen) (10–2000 mg), ibuprofen (10–2000 mg) or any non-steroidal anti-inflammatory drug.

The compositions according to the invention may be administered in any convenient form known to those skilled in the art. These forms include capsules of various types, powders, effervescent formulations, tablets, solutions, suspensions, emulsions and also aerosol sprays. The compositions may be administered orally, enterally, parenterally or transdermally using appropriate technology known to those skilled in the art.

In a further aspect, the present invention provides the use of a vitamin and mineral combination, or the use of any one or two of the components of the combination when for co-administration with the other(s) whether sequentially or simultaneously, in the manufacture of a medicament to combat migraine, said combination comprising therapeutically effective amounts of potassium, vitamin $B_6$ and magnesium. Further ingredients may be optionally included as described above, for example the composition may include an analgesic.

In a yet further aspect, the present invention provides a method of combating migraine, in a person subject to the same, said method comprising administering to said person a composition as described above, the components being given sequentially or simultaneously.

The active ingredients of the composition may be present in combination with any pharmaceutically acceptable carrier and may be in any assimilable form as well known to those skilled in the art for any particular ingredient. One possible carrier is water and in a preferred embodiment the composition is in the form of a tablet which effervesces when placed into water to produce aqueous solution which is then swallowed by the patient. Emulsions and flavoured solutions or suspensions are also possible formulations.

This formula has been tested in volunteer migraine sufferers. When the formula is taken as soon as any premonition symptoms are experienced, many sufferers do not develop the full scale migraine attack they are expecting.

These studies also have demonstrated that the formula, even when it contains no analgesics whatsoever, has a beneficial effect, even if taken after the stage of migraine pain is reached. In some cases, it removed all symptoms, with the exception of a "mild" headache, or greatly reduced the expected severity. For others it completely cleared all symptoms.

The study to date has demonstrated that 70% of the volunteers experienced full relief from debilitating migraine symptoms. A further 20% experienced partial relief, i.e. a reduction of all symptoms except for a mild headache, and for 10% the remedy appeared to have no effect. A number of the volunteers in the 20% partial success category appear to suffer from migraine in the form in which it has few if any premonition symptoms. As a result they were unable to determine when an attach was imminent and could not take the remedy at the optimum time, i.e. before head pain commenced. for those who experience this type of attack, called "common migraine", it is considered that the addition of a simple analgesic would be particularly beneficial.

EXAMPLES

There follow examples of formulas incorporating the invention, the particular form of the actives being merely for illustration. Any appropriate form as well known to those skilled in the art may be used. All figures are in mg and represent a unit dosage form which should be taken as early as possible during an attack. If relief is not obtained within 2 hours, a second dose may be taken, and further doses may be taken later.

|  | 1 | 2 | 3 | 4 | 5 | 6 |
|---|---|---|---|---|---|---|
| Potassium (e.g. as chloride or sulphate) | 400 | 450 | 350 | 600 | 470.0 | 470.0 |
| Magnesium (e.g. as citrate) | 20 | 30 | 30 | 40 | 2.5 | 10 |
| Pyridoxine | 20 | 20 | 15 | 30 | 5 | 10 |
| Calcium (e.g. as citrate) | — | — | — | — | 25.0 | 60.0 |
| Phosphorus (e.g. as dicalcium phosphate) | — | — | — | — | 22.5 | 27.0 |
| Iron (e.g. as sulphate) | — | — | — | — | 0.625 | 0.1 |
| Copper (e.g. as sulphate) | — | — | — | — | 0.05 | 0.5 |
| Zinc (e.g. as citrate) | — | — | — | — | 0.25 | 0.001 |
| Manganese (e.g. as gluconate) | — | — | — | — | 0.25 | — |
| Iodine (e.g. as potassium iodide) | — | — | — | — | — | 0.15 |

To the formula may also be added other vitamins or nutrients such as the following (all figures are in mg):

| Vitamin $B_1$ | 7.5 | 5.0 |
|---|---|---|
| Vitamin $B_2$ | 2.5 | 5.0 |
| Vitamin $B_3$ | 25.0 | 25.0 |
| Vitamin $B_5$ | 5.0 | 10.0 |
| Vitamin $B_{12}$ | 0.0025 | 0.035 |
| Tryptophan | 100 | 500 |
| Folic Acid | 0.15 | 0.2 |
| Biotin | 0.125 | 0.002 |
| Vitamin C | 75.0 | 60.0 |
| Bioflavonoids | 5.0 | 10.0 |

To any of the formulae illustrated above, analgesics may be added such as 1000 mg of aspirin or 1000 mg of ibuprofen or 800 mg of paracetamol. The minerals, vitamins and analgesic may all be presented together or as different components within the same overall package.

As noted above the compositions of the invention are not full dietary supplements or nutritionally complete and the composition claims below do not extend when analgesics are absent to the many published instances of such, comprising besides the minerals and vitamins of the invention many other components and in particular fats, fatty acids and/or fat soluble vitamins.

A specific example is the following two-part formulation, one tablet of each kind:

a) Effervescent Mineral Tablet

| Potassium chloride | 600 mg |
|---|---|
| Potassium bicarbonate | 400 mg |
| Anhydrous citric acid | 800 mg | providing: 470 mg potassium; 285 mg chloride; 787.5 mg citrate

This was tested successfully at full strength and half strength (full strength listed above). A small proportion of sodium salts was present (sodium 2.6 mg).

b) Multi-vitamin Tablet

Magnesium sulphate

Pyridoxine hydrochloride

Phosphorus as dicalcium phosphate

Iron sulphate

Copper sulphate

Zinc sulphate

Manganese sulphate

Iodine as potassium iodide $B_1$ Thiamine mononitrate $B_2$ Riboflavin $B_3$ Nicotinamide $B_5$ pantothenic acid $B_{12}$ cyanocobalamin Tryptophan Folic acid Biotin Vitamin C as ascorbic acid Bioflavonoids The multi-vitamin tablets give the recommended daily intake of components having such recommendation, and in particular 8 mg magnesium and 7.5 mg pyridoxine. Rapid uptake of the potassium was aided by the effervescence of the mineral tablets.

What is claimed is:

1. A method of treating migraine headaches by administering, separately or simultaneously, to a patient subject to migraine headaches 10 to 5000 mg of assimilable potassium, 0.1 to 300 mg pyridoxine and 1 to 1000 mg assimilable magnesium.

2. A method for treating migraine, according to claim 1, by administering said potassium, pyridoxine and magnesium at an early warning stage of a migraine attack.

3. The method of treating migraine according to claim 1 wherein effective amounts of additional minerals and vitamins selected from the group consisting of calcium, phosphorus, iron, copper, zinc, manganese, tryptophan, folic acid, biotin, bioflavonoids and vitamins $B_1$, $B_2$, $B_3$, $B_5$, $B_{12}$ and C are administered to said patient.

4. The method of treating migraine according to claim 1 wherein an effective dose of an analgesic or non-steroidal anti-inflammatory drug is also administered to said patient.

5. The method of treating migraine according to claim 1, wherein the administration of said amounts of assimilable potassium, pyridoxine and assimilable magnesium to said patient is repeated at two-hourly intervals until effective relief from migraine symptoms is obtained.

6. The method of treating migraine according to claim 1, wherein said assimilable potassium is administered by means of an effervescent mineral tablet containing potassium chloride, potassium bicarbonate and anhydrous citric acid; said pyridoxine and assimilable magnesium being separately administered by means of a multi-vitamin tablet containing magnesium sulphate, pyridoxine hydrochloride, dicalcium phosphate, iron sulphate, copper sulphate, zinc sulphate, manganese sulphate, potassium iodide, thiamine mononitrate, riboflavin, nicotinamide, pantothenic acid, cyanocobalamin, tryptophan, folic acid, biotin, ascorbic acid and bioflavonoids.

7. The method of treating migraine according to claim 3, wherein the amounts of said additional minerals and vitamins are in the following ranges:

| | |
|---|---|
| Vitamin $B_1$ | 5.0–7.5 mg |
| Vitamin $B_2$ | 2.5–5.0 mg |
| Vitamin $B_3$ | 25.0 mg |
| Vitamin $B_5$ | 5.0–10.0 mg |
| Vitamin $B_{12}$ | 0.0025–0.035 mg |
| Tryptophan | 100–500 mg |
| Folic Acid | 0.15–0.2 mg |
| Biotin | 0.002–0.125 mg |
| Vitamin C | 60.0–75.0 mg |
| Bioflavonoids | 5.0–10.0 mg |

8. The method of treating migraine according to claim 4 wherein said analgesic dose consists of 1000 mg aspirin.

9. The method of treating migraine according to claim 4 wherein said analgesic dose consists of 1000 mg ibuprofen.

10. The method of treating migraine according to claim 4 wherein said analgesic dose consists of 800 mg paracetamol.

11. A method of treating migraine headaches by administering, separately or simultaneously, to a patient subject to migraine headaches, 100 mg to 1000 mg of assimilable potassium, 1 mg to 100 mg pyridoxine and 10 mg to 500 mg assimilable magnesium.

12. A method of treating migraine headaches by administering, separately or simultaneously, to a patient subject to migraine headaches, 300 mg to 600 mg of assimilable potassium, 4 mg to 30 mg pyridoxine and 20 mg to 300 mg assimilable magnesium.

\* \* \* \* \*